United States Patent [19]

Pierre et al.

[11] Patent Number: 5,300,318
[45] Date of Patent: Apr. 5, 1994

[54] PROCESS FOR POLISHING GRANULATES OF ACTIVE PRINCIPLES

[75] Inventors: Autant Pierre; André Cartillier, both of Commentry, France

[73] Assignee: Rhone-Poulenc Nutrition Animale, Commentry, France

[21] Appl. No.: 835,428

[22] PCT Filed: Jun. 28, 1991

[86] PCT No.: PCT/FR91/00523
  § 371 Date: Apr. 17, 1992
  § 102(e) Date: Apr. 17, 1992

[87] PCT Pub. No.: WO92/00063
  PCT Pub. Date: Jan. 9, 1992

[30] Foreign Application Priority Data
  Jun. 29, 1990 [FR] France ............................... 90 08279

[51] Int. Cl.⁵ .................. B05D 7/00; A23L 1/216; A23B 5/00
[52] U.S. Cl. ........................ 427/212; 427/407.1; 426/96; 426/303; 426/656; 426/807
[58] Field of Search .................... 427/212, 407.1; 426/656, 303, 310, 623, 807, 96, 630

[56] References Cited
FOREIGN PATENT DOCUMENTS
0351760 1/1990 European Pat. Off. .

OTHER PUBLICATIONS
"CRC Handbook of Chemistry and Physics", 60th edition 1979–1980.

*Primary Examiner*—Shrive Beck
*Assistant Examiner*—David M. Maiorana
*Attorney, Agent, or Firm*—Finnegan, Henderson, Farabow, Garrett & Dunner

[57] ABSTRACT

Alimentary and/or medicinal active principles intended for feeding or treating ruminants are polished by spraying a solution of one or more active principles, resins and/or sugars onto the said active principles. The polished active principles are then coated with a polymer providing protection in the rumen.

17 Claims, No Drawings

PROCESS FOR POLISHING GRANULATES OF ACTIVE PRINCIPLES

The present invention relates to the treatment of granulates of active principles, and provides, more particularly, a process for polishing granulates of active principles intended for feeding and/or treating ruminants.

It is known, for example according to U.S. Pat. Nos. 4,181,708, 4,181,709 and 4,181,710, to prepare granulates which are suitable for administration to ruminants, consisting of a core of active substance and of a coating based on a hydrophobic substance and on a polymer which withstands the neutral PH of the rumen but is degradable at the more acidic pH of the abomasum.

In these granulates, the core, consisting of active principle, is granular in form. It is obtained by dry blending the active substances, binders and, optionally, neutralising agents and densifying agents. The blend is then wetted and converted into a pasty mass which is granulated by extrusion at room temperature and prilling. The moist granulate is dried in an oven or fluidised bed, and may then be employed directly for the coating operation. The polymer, hydrophobic substance and fillers are mixed, and the mixture is dispersed in an organic solvent and then sprayed onto the granulate.

To obtain proper protection of the active principle at least 20 g of the mixture of polymer and hydrophobic substance must be sprayed per 100 g of granulated active substance and the coating layer is approximately 150 $\mu$m in thickness (see Example 1 of U.S. Pat. No. 4,181,710).

Since the polymer is expensive, industry has for a long time been searching for a means of reducing its weight percentage in the final granulate, while retaining good protection of the active substance as it passes through the rumen.

This objective has been attained in accordance with the present invention by employing, as the core of active principle subjected to coating, a granulate which has been subjected to an additional polishing operation. A "polishing" operation means an operation which reduces the specific surface area of the granulate by reducing surface nonuniformities. The polished granulate then requires a smaller quantity of coating material for the same quantity of active substance, since the quantity of coating material needed for good protection is related to the specific surface area of the starting granulate.

According to the present invention a granulate of an alimentary and/or medicinal active principle for feeding to or treating ruminants is polished by depositing, more especially by spraying, onto the granulate of active principle a solution of active principles and/or sugars and/or resins. It is preferred to employ an aqueous solution of active principle and especially a solution of sprayed onto a lysine and/or methionine granulate.

The base granulate which is subjected to the polishing operation may be made from lysine hydrochloride crystals or may be prepared according to the operating method of patents U.S. Pat. No. 4,181,708 or U.S. Pat. No. 4,181,710 by mixing one or more active principles in powder form, a binding agent and, optionally, a diluent and/or a filler.

The active principle is generally an amino acid such as methionine, lysine or one of its salts, phenylalanine, histidine, arginine, or tyrosine, a medicament such as a vitamin, antibiotic, or antiparasitic agent, or a protein. The preferred active principle is lysine, in which case a homogeneous granulate is obtained, consisting of a lysine core polished with a lysine film. The diluents and fillers may be sugars, cellulose and/or silica. The binding agent may be a cellulose derivative such as hydroxypropyl methyl cellulose, a resin, or any derivative known in the feedstuff industry for thickening or promoting the preparation of tablets.

The various constituents are granulated by any technique known to a person skilled in the art, for example by extrusion, after wetting, through a die, followed by drying; they may also be subjected to compacting followed by milling.

The granulate obtained is screened so as to retain a granulate distribution between 200 and 4,000 $\mu$m and preferably between 500 $\mu$m and 2,500 $\mu$m.

These granulates have a nonuniform surface and require a large quantity of coating material to protect them during their passage through the rumen. In order to reduce the thickness of the coating layer which is necessary, the nonuniformity of the surface of the granulates has been reduced, using the process of the present invention, by a polishing treatment with the aid of a solution of one of the active principles and/or of sugar and/or of resin.

It is preferred to employ for the polishing operation a solution of lysine hydrochloride which is as concentrated as possible. Thus, a concentration of lysine hydrochloride of between 70 and 150 g per 100 g of water or 40 to 150 g per 100 g of water, which represents a solution containing between 28 and 60% by weight of lysine, is employed in particular. A more dilute solution can be employed within the scope of the present invention. However, any dilution necessitates a longer spraying stage. Thus, for better economy of the process it is preferable to employ a polishing solution which is as concentrated as possible. Since the solubility of lysine increases markedly with temperature, the solution must be maintained at a temperature of between 50° and 70° C. in the case of concentrations which are higher than approximately 50% (that is to say containing at least 100 g of lysine hydrochloride per 100 g of water).

The polishing layer may vary widely in proportions by weight, especially when it consists of an active substance. Thus, a layer whose weight represents between 10 and 150% of the weight of the starting granulate can be employed, but a quantity of between 50 and 110% is preferred, and a quantity of between 70 and 100 is more advantageous when the core consists of lysine hydrochloride crystals.

The thickness of the polishing layer varies with the diameter of the starting granule; for a given percentage by weight of polishing agent, it depends on the diameter, the particle size distribution, and the shape of the granules. It is preferred to employ a polishing layer of thickness between 20 and 200 $\mu$m.

The coating layer which provides protection in the rumen is then sprayed by the technique described in the abovementioned U.S. patents.

The coating contains at least one component which is chosen from basic polymers, copolymers or mixtures whose nitrogen content is between 2 and 14% and whose molecular weight is between 50,000 and 500,000. For the definition of the polymers and copolymers reference is made to their definition in column 7 of U.S. Pat. No. 4,181,710. Among the copolymers it is preferred to employ styrene/2-vinylpyridine copolymers, (containing 50 to 80% by weight of 2-vinylpyridine and 20% to 50% of styrene).

The coating material also contains a hydrophobic substance which is preferably a fatty acid containing 12 to 32 carbon atoms. Suitable hydrophobic substances are also described in U.S. Pat. No. 4,181,710. Stearic acid is preferred.

The preferred coating material for use in the invention has the following composition by weight:
10-30% of 2-vinylpyridine/styrene copolymer
70-90% of stearic acid.

The coating mixture containing the copolymer and the hydrophobic substance is dissolved, e.g. in a halogenated solvent, an alcohol, an ether, a ketone or a mixture of these solvents. It is particularly advantageous to employ an ethanol/1,2-dichloroethane, ethanol/methylene chloride or ethanol/acetone mixture. The coating mixture solution is sprayed onto the polished granulate using a fluidised bed or any other spraying apparatus. It is preferred to employ a spraying apparatus known as spray-coating, Uniglatt type equipped with a Wurster vessel.

The quantity of coating material employed, expressed as solids in relation to the polished granulate, is especially between 10 and 30%, and preferably between 15 and 25%, by weight which represents a coating thickness of between 20 and 70 µm in the case of granules with a mean diameter of between 500 µm and 1,400 µm.

The granulates obtained after coating exhibit a stability towards the neutral pH of the rumen which is improved when compared with the granulates of the prior art which have not been subjected to a polishing operation.

The present invention is illustrated by the following Examples.

EXAMPLE I GRANULATION

Preparation of Lysine Hydrochloride Granulate by Extrusion and Prilling

Equipment Used

Mixer of 50 l capacity (planetary system)
Pharmex 45 extruder
Sphaeromat 400 priller
Fluidised bed drier.

Raw Materials

Lysine hydrochloride milled in the Forplex mill 400 µm in diameter
Hydroxypropyl methyl cellulose
Avicel microcrystalline cellulose Operating Method a) Dough preparation
Into the mixer are introduced:

| lysine hydrochloride 400 µm in diameter | 2550 g |
|---|---|
| microcrystalline cellulose | 450 g |

These are homogenised dry for 1 minute. An aqueous solution of binder is introduced, prepared beforehand and made up of:

| water | 1227.9 g |
|---|---|
| hydroxypropyl methyl cellulose | 92.1 g |

When the addition is complete, these are stirred for 1 minute 30 seconds.

b) Extrusion

The dough obtained is extruded with the aid of the Pharmex 45 extruder equipped with a 0.8 mm diameter die—speed of rotation of the screw 90 rev/min.

c) Prilling

All the extrudate is immediately introduced into the rotating priller—speed 1,000 rev/min—treatment time: 2 min.

d) Fluidised bed drying
Air temperature: 60° C.

e) Particle size distribution of the prills obtained

| diameter ≦ 0.5 mm | 13.8% |
|---|---|
| 0.5 < diameter ≦ 0.63 mm | 8.4% |
| 0.63 < diameter ≦ 0.8 mm | 16.2% |
| 0.8 < diameter ≦ 1 mm | 28.1% |
| 1 < diameter ≦ 1.25 mm | 19.3% |
| 1.25 < diameter ≦ 1.25 mm | 14.2% |

*This fraction of diameter above 1.25 mm includes the agglomerates originating from the drying.

EXAMPLE 2 POLISHING

Operating Method of the Polishing 400 g of the particles to be treated (granules from Example 1) with a diameter of between 0.63 and 0.80 mm are introduced into the Uniglatt apparatus. Fluidisation is set in motion and the tested polishing solution is sprayed.

After polishing, the product is collected and the coating operation is carried out on 350 g of polished particles, as described below.

Preparation of the Polishing Solutions

The desired quantity of lysine monohydrochloride (99.9% assay) is dissolved in distilled water at approximately 30° C. The lysine hydrochloride content is limited by its solubility in water.

Apparatus Settings

All the polishing operations were carried out under the following conditions:

| granule charge | 400 g |
|---|---|
| fluidisation air flow | 100 m³/h |
| air entry temperature | 40° C. |
| spraying pressure | 1.5 bar |
| rate of spraying of the polishing solution | 14 ml/min |
| solution temperature | 30° C. |

EXAMPLE 3 COATING

Coating Equipment

Glatt Uniglatt type spray-coating apparatus 5-inch Wurster vessel.

Operating Method for Coating

Coating Solution

| Composition per 100 g of solution: | |
|---|---|
| 2-vinylpyridine-styrene (70-30) copolymer | 1.93 g |
| pure stearic acid | 7.74 g |
| ethanol | 35.06 g |
| 1,2-dichloroethane | 55.26 g |
| Fluidised bed settings: | |
| charge of particles 0.63–0.80 mm in diameter | 350 g |
| fluidisation air flow | 100 Nm³/h |
| air entry temperature | 30° C. |
| rate of spraying of the coating solution | 11 ml/min |
| spraying air pressure | 1.5 bar |
| coating solution temperature | 40° C. |

Operating Method

The particles to be coated are charged into the Uniglatt vessel. Fluidisation is set in motion and spraying of the coating solution is commenced. Samples of approximately 10 g of product are taken after spraying of:
362 g of solution corresponding to 35 g of solids, i.e., a 10% coating ratio;
724 g of solution corresponding to 70 g of solids, i.e., a 20% coating ratio;
1086 g of solution corresponding to 105 g of solids, i.e., a 30% coating ratio.
The coating ratio is defined as the weight of solids sprayed onto 100 g of initial particles.

The lysine HCl release rate is determined on each sample (see Table 1).

EXAMPLE 4

A test comparable with Tests 1, 2 and 3 was carried out with lysine hydrochloride which, after granulation, had a diameter of:
- 0.5 to 0.63 mm
- 0.63 to 0.80 mm
- 0.80 to 1.0 mm
- 1.0 to 1.4 mm in the case of a polishing ratio of 40 g of lysine hydrochloride per 100 g of granules. The results reported in Table 2 prove that the protection is markedly easier at an equivalent and low (10%) coating ratio when the granulate is larger in diameter.

EXAMPLE 5

Example 4 is reproduced with a polishing ratio of 10% and various thicknesses of coating material. The results are expressed in Table 3.

EXAMPLE 6

Examples 2 and 3 are reproduced, but the granulate based on lysine hydrochloride, microcrystalline cellulose and hydroxypropyl methyl cellulose is replaced with particles of lysine hydrochloride which are merely screened between 0.63 and 0.80 mm. The polishing and the coating are carried out with the solutions described in these examples.

Table 4 shows, in the same way as Table 1, the results of the rates of release of lysine hydrochloride.

TABLE 1

POLISHING OF GRANULATES WITH LYS./HCl SOLUTION
EFFECT ON THE QUALITY OF THE COATING

| TEST NO. | POLISHING water ml/ 100 g core | POLISHING Lys g/ 100 g core | Diam. after. pol. μm | COATING RATIO g % g core | COATING THICKNESS μm | RELEASE pH 6/24 h % | RELEASE pH 6/5 h % |
|---|---|---|---|---|---|---|---|
| C1 | 0 | 0 | 715 | 10 | 14.4 | 88.8 | 49.1 |
|  |  |  |  | 20 | 27.8 | 25.4 | 7 |
|  |  |  |  | 30 | 40.4 | 8.5 | 0 |
| C2 | 50 | 0 | 715 | 10 | 14.4 | 100 | 88.6 |
|  |  |  |  | 20 | 27.8 | 45.9 | 12 |
|  |  |  |  | 30 | 40.4 | 13.5 | 0 |
| 1 | 50 | 10 | 738 | 10 | 14.9 | 31.2 | 11.3 |
|  |  |  |  | 20 | 28.9 | 3.5 | 0 |
|  |  |  |  | 30 | 41.7 | 0 | 0 |
| 2 | 50 | 20 | 760 | 10 | 15.4 | 18.4 | 5.4 |
|  |  |  |  | 20 | 29.6 | 2.6 | 0 |
|  |  |  |  | 30 | 42.9 | 2.5 | 1.2 |
| 3 | 25 | 10 | 738 | 10 | 14.9 | 50.2 | 30.3 |
|  |  |  |  | 20 | 28.9 | 10.8 | 4.3 |
|  |  |  |  | 30 | 41.7 | 4.5 | 0 |
| 4 | 12.5 | 10 | 738 | 10 | 14.9 | 55.5 | 28.6 |
|  |  |  |  | 20 | 28.9 | 11.1 | 3.3 |
|  |  |  |  | 30 | 41.7 | 6.2 | 0 |

TABLE 2

EFFECT OF THE INITIAL PARTICLE SIZE

Composition of the polishing solution:

| water | 100 | g % g initial |
| lysine HCl | 40 | particles |

| TEST NO. | INITIAL PARTICLE SIZE mm | Mean diam. after polishing mm | COATING RATIO* | COATING THICKNESS μm | RELEASE pH 6/24 h |
|---|---|---|---|---|---|
| 1 | 0.5–0.63 | 0.63 | 10 | 12 | 84.9 |
|  |  |  | 20 | 23 | 6 |
|  |  |  | 30 | 33 | 4.3 |
| 2 | 0.63–0.8 | 0.8 | 10 | 15 | 40 |

TABLE 2-continued

EFFECT OF THE INITIAL PARTICLE SIZE

Composition of the polishing solution:

| water | 100 | g % g initial |
| lysine HCl | 40 | particles |

| TEST NO. | INITIAL PARTICLE SIZE mm | Mean diam. after polishing mm | COATING RATIO* | COATING THICKNESS μm | RELEASE pH 6/24 h |
|---|---|---|---|---|---|
|  |  |  | 20 | 29 | 0 |
|  |  |  | 30 | 42 | 0.8 |
| 3 | 0.8–1.0 | 1 | 10 | 19 | 44.4 |
|  |  |  | 20 | 36 | 4.6 |
|  |  |  | 30 | 52 | 2.3 |
| 4 | 1.0–1.4 | 1.34 | 10 | 25 | 21.7 |
|  |  |  | 20 | 48 | 6.3 |
|  |  |  | 30 | 70 | 6.7 |

*g coating material % g polished particles

TABLE 3

EFFECT OF THE INITIAL PARTICLE SIZE

"Low" polishing
Composition of the polishing solution:

| water | 50 | g % g initial |
| lysine HCl | 10 | particles |

| TEST NO. | INITIAL PARTICLE SIZE mm | Mean diam. after polishing mm | COATING RATIO* | COATING THICKNESS μm | RELEASE pH 6/24 h |
|---|---|---|---|---|---|
| 1 | 0.5–0.63 | 0.58 | 10 | 11 | 100 |
|  |  |  | 20 | 21 | 11.2 |
|  |  |  | 30 | 30 | 3.6 |
| 2 | 0.63–0.8 | 0.74 | 10 | 14 | 97.8 |
|  |  |  | 20 | 27 | 7.2 |
|  |  |  | 30 | 39 | 2.4 |
| 3 | 0.8–1.0 | 0.98 | 10 | 18 | 71.8 |
|  |  |  | 20 | 35 | 7.6 |
|  |  |  | 30 | 51 | 3.5 |
| 4 | 1.0–1.4 | 1.24 | 10 | 23 | 63.3 |
|  |  |  | 20 | 45 | 13.3 |
|  |  |  | 30 | 65 | 9.8 |

*g coating material % g polished particles

TABLE 4

POLISHING OF LYSINE PARTICLES WITH LYS./HCl SOLUTION EFFECT ON QUALITY OF COATING

| TEST NO. | POLISHING water ml/ 100 g core | POLISHING Lys g/ 100 g core | Diam. after. pol. μm | COATING RATIO g % g core | COATING THICKNESS μm | RELEASE pH 6/24 h % | RELEASE pH 6/5 h % |
|---|---|---|---|---|---|---|---|
| C1 | 50 | 0 | 715 | 10 | 14.4 | 100 | 94.9 |
|  |  |  |  | 20 | 27.9 | 37.8 | 16.9 |
|  |  |  |  | 30 | 40.2 | 19.1 | 7.5 |
| 1 | 25 | 10 | 738 | 10 | 14.9 | 98.8 | 43.9 |
|  |  |  |  | 20 | 28.8 | 19.7 | 8 |
|  |  |  |  | 30 | 41.7 | 12.1 | 4.7 |
| 2 | 25 | 20 | 760 | 10 | 15.4 | 100 | 33.8 |
|  |  |  |  | 20 | 29.6 | 22.6 | 5.8 |
|  |  |  |  | 30 | 42.9 | 9.1 | 2.3 |
| 3 | 12.5 | 10 | 738 | 10 | 14.9 | 96 | 44.6 |
|  |  |  |  | 20 | 28.9 | 28.1 | 10.9 |
|  |  |  |  | 30 | 41.7 | 16.1 | 4.9 |
| 4 | 50 | 20 | 760 | 10 | 15.4 | 100 | 57.6 |
|  |  |  |  | 20 | 29.6 | 29.6 | 12.8 |
|  |  |  |  | 30 | 42.9 | 21.8 | 5 |
| 5 | 31.2 | 25 | 770 | 10 | 15.6 | 78.9 | 18.9 |
|  |  |  |  | 20 | 30 | 22.9 | 6.1 |
|  |  |  |  | 30 | 43.5 | 9.1 | 2.1 |
| 6 | 62.5 | 50 | 818.5 | 10 | 16.55 | 35.8 | 10.8 |
|  |  |  |  | 20 | 31.9 | 13.9 | 2.3 |
|  |  |  |  | 30 | 46.3 | 8.7 | 1.7 |
| 7 | 93.7 | 75 | 861.6 | 10 | 17.4 | 21.5 | 6 |
|  |  |  |  | 20 | 33.6 | 2.7 | 0 |
|  |  |  |  | 30 | 48.7 | 0 | 0 |

We claim:

1. A process for polishing a granulate for feeding or treating ruminants, said granulate containing lysine or a salt of lysine, said process comprising the step of:

spraying onto said granulate a solution containing lysine or a salt of lysine at a concentration of 40g to 150g per 100g of water to obtain a polished granulate.

2. A process according to claim 1, wherein said solution sprayed is lysine hydrochloride and further wherein said granulate contains lysine hydrochloride crystals.

3. A process according to claim 3, wherein said solution sprayed contains lysine or a salt of lysine at a concentration of 70 to 150 g per 100 g of water.

4. A process according to claim 1, in which said salt of lysine sprayed onto said granulate is lysine hydrochloride in solution at a concentration higher than 100 g per 100 ml of water and is maintained at a temperature of from 50° to 70° C. while it is sprayed onto said granulate.

5. A process according to claim 4, in which said solution of lysine hydrochloride is sprayed onto said granulate, in such quantity that the quantity of lysine hydrochloride sprayed onto said granulate, and expressed as solids relative to the starting granulate, is from 10 to 150% by weight.

6. A process according to claim 5, in which said quantity is from 25 to 110%.

7. A process according to claim 6, in which said quantity is from 70 to 100%.

8. A process according to claim 1 wherein said polished granulate obtained by said spraying step is thereafter coated with a coating layer which provides protection to said granulate in the rumen and is degradable in the abomasum of a ruminant.

9. A granulate of lysine or a salt of lysine, produced according to the process of claim 1.

10. A granulate of lysine or a salt of lysine produced according to the process of claim 8.

11. A granulate according to claim 9, comprising 50% to 90% by weight of lysine or a salt of lysine provided in the starting granulate and 10% to 50% by weight of lysine or a salt of lysine provided by said step of spraying.

12. A granulate according to claim 11, having a particle size of from 0.5 to 2.5 mm.

13. A granulate according to claim 9 which after polishing, is coated with one or more polymers or copolymers containing basic amino groups optionally mixed with a hydrophobic substance to form a coating layer on said granulate.

14. A granulate according to claim 10 which after polishing, is coated with one or more polymers or copolymers containing basic amino groups optionally mixed with a hydrophobic substance to form a coating layer on said granulate.

15. A granulate according to claim 14 wherein said copolymer is based on vinylpyridine and styrene and is combined with stearic acid.

16. A granulate according to claim 14, in which the weight quantity of said coating layer is from 10 to 30% based on the weight of said granulate.

17. A granulate according to claim 14 in which said coating layer is 20 to 70 μm in thickness.

* * * * *

UNITED STATES PATENT AND TRADEMARK OFFICE
CERTIFICATE OF CORRECTION

PATENT NO. : 5,300,318
DATED : April 05, 1994
INVENTOR(S) : Pierre Autant et al.

It is certified that error appears in the above-indentified patent and that said Letters Patent is hereby corrected as shown below:

On the title page, item [19] should read --Autant et al.--

On the title page, item [75] Inventors:
should read -- Pierre Autant--.

Claim 3, column 9, line 12, "3" should read --1--.

Signed and Sealed this

Second Day of May, 1995

Attest:

BRUCE LEHMAN

Attesting Officer

Commissioner of Patents and Trademarks